United States Patent [19]

Desjardins et al.

[11] Patent Number: 4,530,367
[45] Date of Patent: Jul. 23, 1985

[54] APPARATUS FOR MEASURING FACIAL SWELLING

[75] Inventors: Paul J. Desjardins, Maplewood, N.J.; Sathischandran Menon, Zion, Ill.; Maano Milles, Berkeley Heights; Hans E. Pawel, Maplewood, both of N.J.

[73] Assignees: N.J. Institute of Technology; University of Medicine and Dentistry, both of Newark, N.J.

[21] Appl. No.: 532,736

[22] Filed: Sep. 15, 1983

[51] Int. Cl.³ .............................................. A61B 5/10
[52] U.S. Cl. ..................................... 128/777; 33/124
[58] Field of Search ........................ 128/774, 776, 777; 33/1 V, 121, 122, 123, 124, DIG. 5

[56] References Cited

U.S. PATENT DOCUMENTS

| 3,061,936 | 11/1962 | Dobbeleer . | |
| 3,154,673 | 10/1964 | Edwards | 33/1 V |
| 3,256,523 | 6/1966 | Pietro . | |
| 3,624,684 | 11/1971 | McCuslin | 33/124 |
| 3,652,842 | 3/1972 | Lewis | 33/123 X |
| 3,722,103 | 3/1973 | Gregoire . | |
| 3,885,318 | 5/1975 | Whitehouse et al. . | |
| 3,955,073 | 5/1976 | Carew et al. | 33/1 V |
| 4,135,498 | 1/1979 | McGee . | |
| 4,328,620 | 5/1982 | Mack et al. . | |
| 4,383,535 | 5/1983 | Schorr | 128/777 |
| 4,459,109 | 7/1984 | Radke | 128/777 |

FOREIGN PATENT DOCUMENTS 2042719 9/1980 United Kingdom .................. 33/1 V

OTHER PUBLICATIONS

Lokken, P. et al., "Bilateral Surgical Removal of Impacted Lower Third Molar Teeth as a Model for Drug Evaluation: A Test with Ibuprefen", Europ. J. Clin. Pharmacol., 8, 209-216, (1975), pp. 209-216.
Dixon, D. A., "Minimal Forms of the Cleft Syndrome Demonstrated by Stereophotogrammetric Surveys of the Face", Brit. Dent. J., Mar. 7, 1972, pp. 183-189.
Linenberg, W. B., "The Clinical Evaluation of Dexamethasone in Oral Surgery", Oral Surgery, Oral Medicine and Oral Pathology, vol. 20, No. 1, Jul. 1965, pp. 6-28.
Sowray, J. H., "An Assessment of the Value of Lyophilised Chymotrypsin in the Reduction of Post-Operative Swelling Following the Removal of Impacted Wisdom Teeth", Brit. Dent. J., Feb. 21, 1961, pp. 130-133.
Cameron, I. W., "An Investigation Into Some of the Factors Concerned in the Surgical Removal of the Impacted Lower Wisdom Tooth, Including a Double Blind Trial of Chymoral", Brit. J. of Oral Surgery, (1980), 18:112-124, pp. 112-124.

Primary Examiner—Edward M. Coven
Attorney, Agent, or Firm—David A. Jackson; Daniel H. Bobis

[57] ABSTRACT

Apparatus for measuring a volume change for facial swelling of a person which may occur after surgical removal of wisdom teeth, including a bite fork engageable within the mouth of the person for providing a relatively fixed reference position for the facial swelling; a reciprocable feeler rod having a free end with a feeler wheel secured thereto and reciprocable in a first x-axis direction substantially normal to the facial swelling; a spring which biases the feeler wheel into contact with the facial swelling; a tracing device for moving the feeler wheel in a second y-axis direction substantially normal to the first direction to cause the feeler wheel to trace across the facial swelling in a plurality of parallel planes spaced apart by a predetermined distance in the z-axis direction; a first LVDT for producing a first signal in response to the reciprocable movement of the feeler wheel in the first direction; a second LVDT for producing a second signal in response to movement of the feeler wheel in the second direction; and a differential volume circuit for producing an output signal corresponding to the volume change in response to the first signal, the second signal and the predetermined distance.

11 Claims, 4 Drawing Figures

APPARATUS FOR MEASURING FACIAL SWELLING

BACKGROUND OF THE INVENTION

This invention relates generally to measuring apparatus and, more particularly, is directed to apparatus for measuring facial swelling of a patient which may occur after surgical removal of wisdom teeth.

The surgical extraction of impacted wisdom teeth is followed almost invariably by some degree of post-operative swelling of the related soft tissues. Various anti-inflamatory drugs have been utilized for reducing such swelling. In order to assess the anti-inflamatory effects of these drugs, it is necessary to measure the extent that the swelling is reduced over a period of time. However, one of the major difficulties in investigations of facial swelling is that of accurately measuring the swelling. With the measuring techniques utilized to date, pre-operative and post-operative measurements are taken and the results are compared to obtain an indication of the extent of swelling.

Several measurement techniques have been employed to assess swelling following surgery, including stereophotogrammetry and contrast radiography. The stereophotogrammetric technique is disclosed in an article, D. A. Dixon et al., "Minimal Forms of the Cleft Syndrome Demonstrated by Stereophotogrammetric Surveys of the Face", British Dental Journal, Mar. 7, 1972, pgs. 183–189. In addition to the above techniques, clinical analysis, that is, observation of the patient, has also been utilized to determine the extent of swelling. William B. Linnenberg, "The Clinical Evaluation of Dexamethasone in Oral Surgery", Oral Surgery, Oral Medicine and Oral Pathology, Vol. 20, No. 1, 1965, pgs. 6–28.

Still further, mechanical techniques for measurement of swelling have been utilized. For example, with one mechanical method, one arm of a pair of callipers is placed in the interdental space between the mandibular first and second molars and the other arm of the callipers is placed in light contact with the external cheek surface. J. H. Sowray, "An Assessment of the Value of Lyophilised Chymotrypsin in the Reduction of Post-Operative Swelling Following the Removal of Impacted Wisdom Teeth", British Dental Journal, Feb. 21, 1961, pgs. 130–133. However, utilization of callipers does not provide an accurate measurement of the extent of swelling since such measurement is taken at a single point on the cheek. A similar mechanical technique is desribed in the article "An Investigation into Some of the Factors Concerned in the Surgical Removal of the Impacted Lower Wisdom Tooth, including a Double-Blind Trial of Chymoral", by Ian W. Cameron, published in the British Journal of Oral Surgery (1980) 18, pgs. 112–124. However, as recognized on page 121 of this article, the device used therein is only capable of measuring the maximum lateral extension of the swelling of the cheek. It is to be noted that the latter article at page 121 indicates that a volume measurement would be a true measure of post-operative oedema, but further indicates that no such measurement seems possible unless using a very sophisticated stereophotogrammetric technique.

Another mechanical technique that has been utilized is described in the article, P. Lokken, "Bilateral Surgical Removal of Impact Lower Third Molar Teeth as a Model for Drug Evaluation: A Test for Ibuprofen", Europ. J. clin. Pharmacol. 8, pgs. 209–216, 1975. The device of this latter article consists of 16 adjustable plastic screws, eight on each side of the face, on bilateral plates, which are fixed on a facial bow attached to an individual bite-block. The plastic screws are adjusted into touching contact with the skin and are adjusted at each sitting and then compared with pre-operative measurements to give an indication of swelling. However, again, with this device, only point measurements are taken.

OBJECTS AND SUMMARY OF THE INVENTION

Accordingly, it is an object of the present invention to provide apparatus for measuring a volume change for facial swelling of a person.

It is another object of the present invention to provide apparatus for measuring volume change for facial swelling of a person by tracing the skin contour of the swelling in a series of spaced parallel planes.

In accordance with an aspect of the present invention, apparatus for measuring a volume change for facial swelling of a person, includes bite fork means engageable within the mouth of the person for providing a relatively fixed reference position for the facial swelling; reciprocable means having a free end and reciprocable in a first direction substantially normal to the facial swelling; biasing means for maintaining the free end of the reciprocable means in communication with the facial swelling; scanning means for moving the reciprocable means in a second direction substantially normal to the first direction to cause the free end to trace across the facial swelling in a plurality of parallel planes spaced apart by a predetermined distance; first output means for producing a first signal in response to the reciprocable movement of the reciprocable means in the first direction; second output means for producing a second signal in response to movement of the free end in the second direction; and differential volume means for producing an output signal corresponding to the volume change in response to the first signal, the second signal and the predetermined distance.

The above, and other, objects, features and advantages of the present invention will become readily apparent from the following detailed description thereof which is to be read in connection with the accompanying drawings.

DETAILED DESCRIPTION OF A PREFERRED EMBODIMENT

Figure 1:
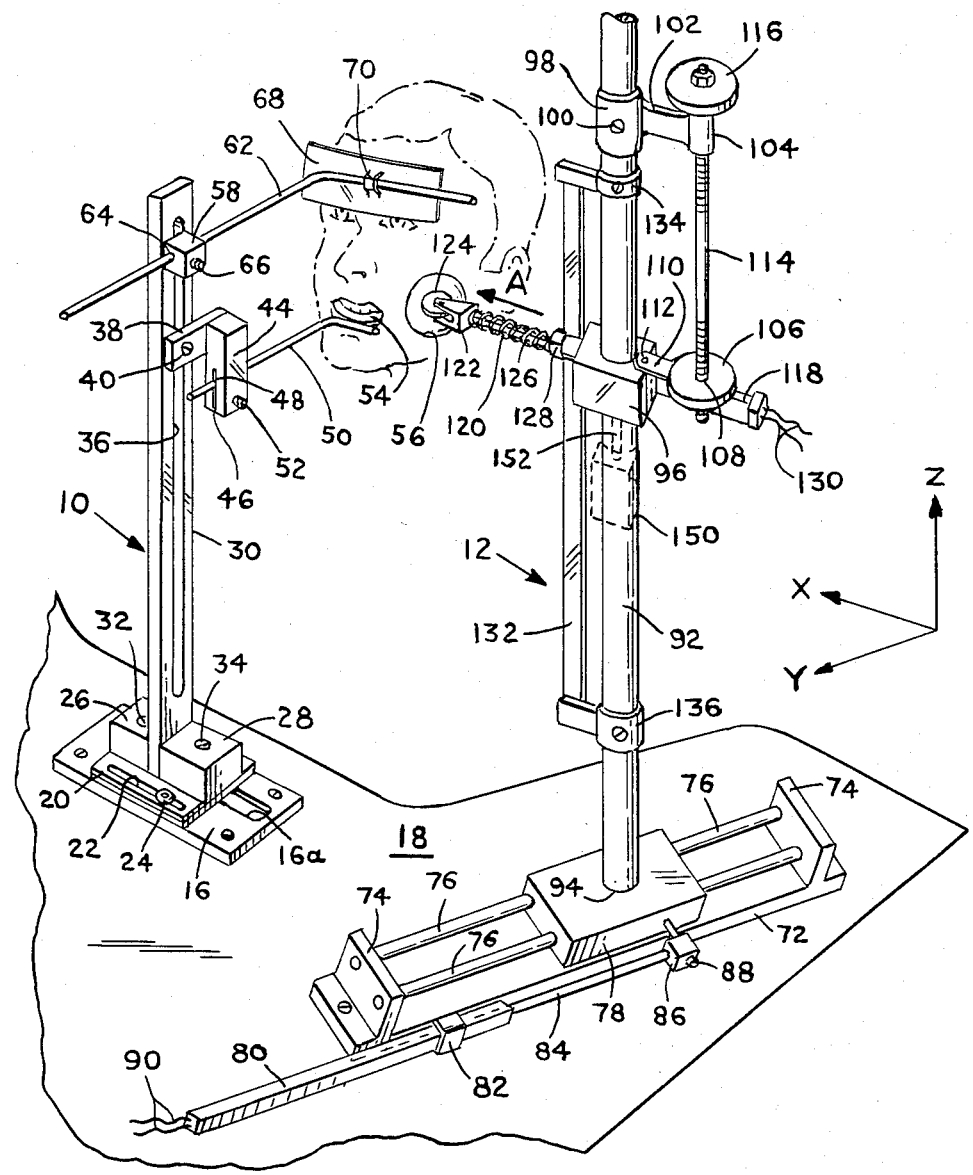
FIG. 1 is a perspective view of apparatus for measuring facial swelling according to the present invention.

Referring to the drawings in detail, and initially to FIG. 1 thereof, the apparatus according to the present invention generally includes a stabilizing device 10 which fixes the head of the patient at a predetermined position, a tracing device 12 which traces along a facial contour and circuitry (FIG. 4) which produces an output signal corresponding to a post-operative reference change in respect to a pre-operative reference measurement, in response to respective output signals from tracing device 12.

More particularly, stabilizing device 10 includes a base plate 16 fixedly mounted substantially at the center of a support 18 by means of screws, bolts or the like. Base plate 16 is of an elongated rectangular configuration and includes a center longitudinal track 16a. A slide 20 is mounted on base plate 16 for slidable movement with respect thereto. In this regard, the underside of slide 20 may include a pin (not shown) which is engageable within center longitudinal track 16a such that slide 20 is slidably movable along track 16a. In order to fix the position of slide 20 along track 16a, slide 20 is provided with a longitudinal slot 22 through which a bolt 24 from base plate 16 extends and which can be tightened to lock slide 20 at a fixed position along track 16a.

Figure 2:
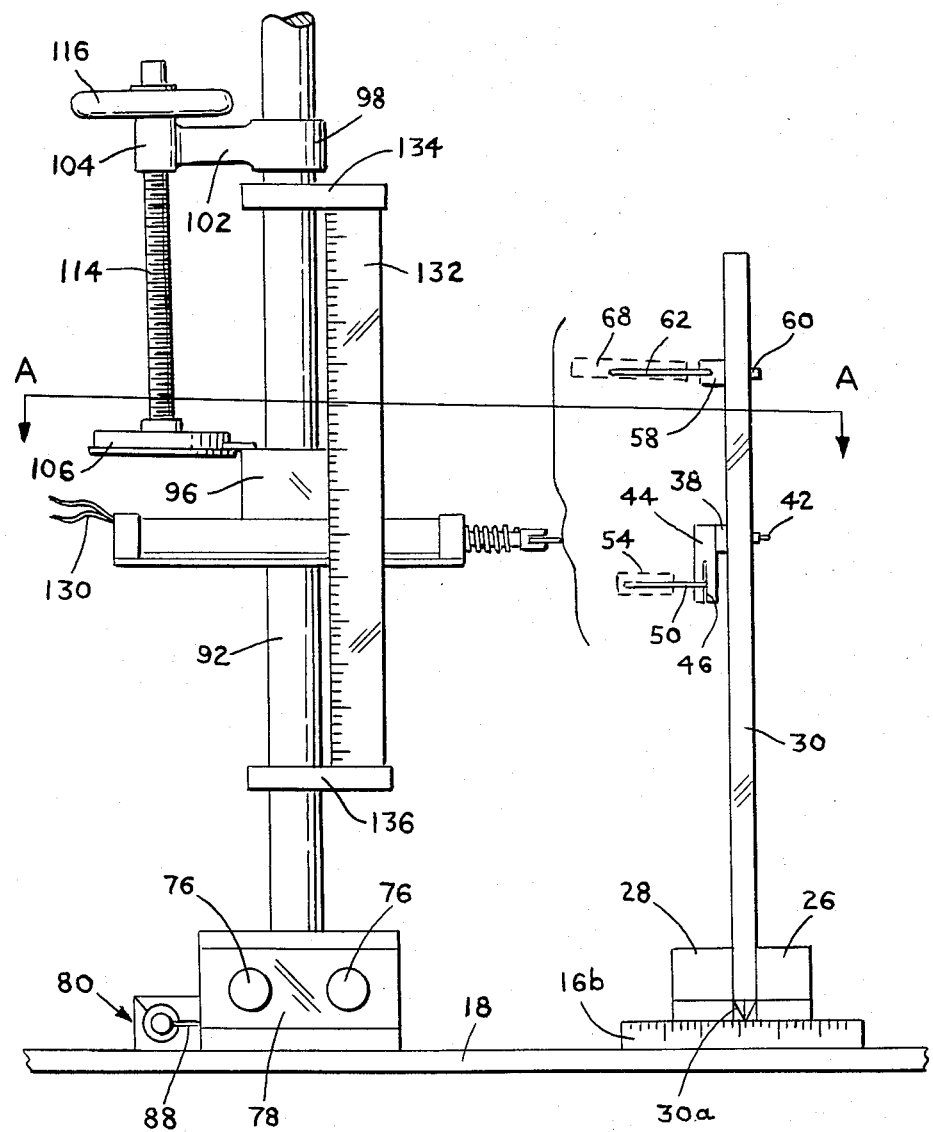
FIG. 2 is a front plan view of the apparatus of FIG. 1.

A pair of blocks 26 and 28 are secured to the upper surface of slide 20 for supporting a bite fork post 30. More particularly, blocks 26 and 28 are removably mounted on the surface of slide 20 by any suitable means, such as bolts 32 and 34, respectively, and define a space therebetween in which bite fork post 30 is tightly held between blocks 26 and 28. Bite fork post 30 is a relatively thin elongated member which extends upright from the surface of slide 20, between blocks 26 and 28, and includes a center longitudinal slot 36. As shown in FIG. 2, the front lower end of bite fork post 30 has a pointer 30a thereon which points to a measurement on the scale 16b positioned on the front face of base plate 16 so that accurate positioning of slide 20 in slot 16a can be obtained.

Figure 3:
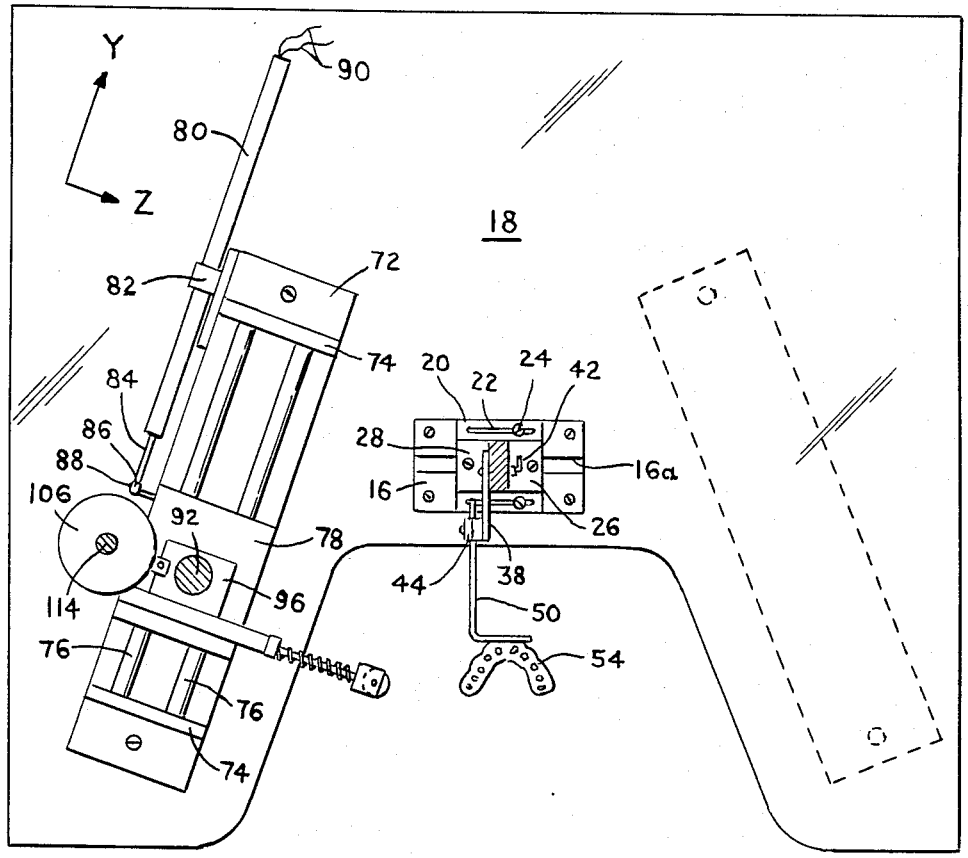
FIG. 3 is a top plan view of the apparatus of FIG. 2, taken along line A—A thereof.

A slidable member 38 is slidably mounted on bite fork post 30 with respect to slot 36 by means of a bolt 40 extending through slot 36 and which may be tightened to fix slidable member 38 at any position along bite fork post 30. In this regard, accurate measurement of the vertical position of slidable member 38 can be achieved by a pointer 42 (FIG. 3), extending from bolt 40 at the opposite side of bite fork post 30 and which indicates the height or vertical position of slidable member 38 in relation to a vertical scale (not shown) on the opposite side of bite fork post 30. A bite fork clamp 44 of a rectangular block configuration is secured to slidable member 38 and includes a center longitudinal slit 46 which extends at least along a portion of clamp 44 and to one end thereof. In this manner, the lower ends of bite fork clamp 44 on either side of slit 46 can be separated slightly. An aperture 48 extends through bite fork clamp 44 along center longitudinal slit 46 and through which an L-shaped rod 50 extends, and accordingly, a bolt 52 is provided at the lower end of block 44 normal to the plane of slit 46 and at a position lower than aperture 48 to tighten the two lower halves of clamp 44 adjacent slit 46 together so as to secure L-shaped rod 50 within aperture 48 at a predetermined location. In other words, L-shaped rod 50 is positioned within aperture 48 and slidable therein to a predetermined position, whereupon bolt 52 is tightened to lock or restrain L-shaped rod 50 at such position. As shown in FIG. 3, a bite fork 54 which is previously formed for the particular patient is secured to L-shaped rod 50. Accordingly, when bite fork 54 is inserted within the mouth of a patient and the patient bites down upon bite fork 54, the lower part of the patient's head is fixed, whereupon any facial swelling 56 is also fixed to a reference position. In this regard, a relatively fixed reference position for facial swelling 56 is provided so that measurements of such facial swelling may be readily taken. It is to be appreciated that the height of bite fork 54 can readily be changed for each patient, with pointer 42 always providing an indication of such height. In addition, lateral movement of bite fork 54 can be readily achieved by movement of slide 20 within center longitudinal track 16a and this position can always be accurately determined for the same patient by means of pointer 30a and scale 16b.

In addition, in order to ensure accurate positioning of facial swelling 56, a support block 58 is also slidably mounted adjacent bite fork post 30 with respect to longitudinal slot 36. Support block 58 is positioned above slidable member 38 and may be fixed at any relative position above slidable member 38 by means of a bolt 60 extending through slot 36. An L-shaped rod 62 is positioned within an aperture 64 of support block 58, in much the same manner as L-shaped rod 50 within bite fork clamp 44. Accordingly, L-shaped rod 62 is slidable within aperture 64 and can be locked at any desired position by a set screw 66 within support block 58. A forehead support 68 is provided at the free end of L-shaped rod 62 and includes a U-shaped bracket 70 within which L-shaped rod 62 is inserted such that forehead support 68 is adapted to swivel about L-shaped rod 62. In this manner, the lower portion of the patient's head is fixed by bite fork 54, while the upper portion of the patient's head is fixed by forehead support 68 so that a relatively fixed reference position for the facial swelling 56 is provided.

Once the head is stabilized by stabilizing device 10, a measuring operation can be performed by tracing device 12. As shown in the figures, tracing device 12 includes a base plate 72 secured to support 18 by bolts, screws or the like. Base plate 72 includes two vertical or upstanding supports 74 at opposite ends thereof, which support two parallel spaced support rods 76 which extend therebetween. A slide 78 is provided with support rods 76 extending therethrough such that slide 78 is slidable in the direction along rods 76, that is, in the y-direction of FIG. 1. A y-axis linear variable differential transformer (LVDT) 80 is secured to one side of base plate 72 by means, for example, of a housing 82 secured to base plate 72. LVDT 80 includes a reciprocable rod 84 with an enlarged head 86 at the free end thereof which is secured to slide 78, for example, by means of a bolt 88 extending through enlarged head 86. In this regard, as slide 78 moves along support rods 76, LVDT 80 provides an output signal at output terminals 90 thereof which corresponds to the position of slide 78 along the y-axis. It is to be appreciated that slide 78 may be moved manually along support rod 76 or a motor (not shown) may be provided for performing this operation.

A support rod 92 is vertically mounted within a bore 94 of slide 78, and an adjustable support block 96 is slidably mounted on rod 92. A device for adjusting and locking the vertical position of support block 96 with respect to rod 92 includes a sleeve 98 which is fixed to an upper portion of rod 92 by a set screw 100. An arm 102 extends radially outward from sleeve 98 and has another sleeve 104 secured to the free end thereof, sleeve 104 having a screw-threaded bore (not shown). A disc 106 also having a screw-threaded bore 108 is secured to adjustable support block 96, for example, by an arm 110 integral with disc 106 and which is secured to support block 96 by a bolt 112. The positions of sleeve 104 and disc 106 are such that the screw-threaded bores thereof are in vertical alignment. In this regard, a screw-threaded shaft 114 is screw-threadedly received within the bores of sleeve 104 and disc 106, with an adjustment wheel 116 being secured to shaft 114 at the upper end thereof at a position above sleeve 104. Since sleeve 104 has its vertical position fixed by sleeve 98 secured to rod 92, rotation of adjustment wheel 116 results in adjustable support block 96 moving vertically along rod 92 so that the vertical position thereof can be readily adjusted.

In accordance with the present invention, a linear variable differential transformer (LVDT) 118 is secured at one side of support block 96 and includes a feeler rod 120 which is reciprocable along the x-axis of FIG. 1. A bifurcated element 122 is connected to the free end of feeler rod 120 and a feeler wheel 124 is rotatably mounted between the legs of bifurcated element 122. In addition, a compression spring 126 surrounds feeler rod 120 between bifurcated element 122 and the housing of LVDT 118 so as to normally bias feeler wheel 124 in the direction of arrow A of FIG. 1. In other words, feeler wheel 124 is biased into engagement with facial swelling 56. In this regard, as feeler wheel 124 traverses the contour of facial swelling 56 and thereby moves along the x-axis, LVDT 118 provides an output signal corresponding to the x-axis movement, at output terminals 130 thereof.

In accordance with the present invention, feeler wheel 124 is caused to trace the contour of facial swelling 56 in a plurality of x-y planes which are separated by a predetermined distance, for example, every 0.5 cm. in the vertical direction, that is, along the z-axis of FIG. 1. For example, with feeler wheel 124 having its vertical position fixed along the z-axis, slide 78 is moved along support rods 76, that is, along the y-axis and an output signal is obtained at output terminals 90 of LVDT 80 in response thereto. During such movement, feeler wheel 124 is biased into engagement with the surface of facial swelling 56 and is caused to reciprocate along the x-axis in accordance with the amount of swelling, while it also traverses the swelling in the direction of the y-axis. An output corresponding to movement of feeler wheel 124 along the x-axis is obtained at output terminals 130 of LVDT 118. Thereafter, adjustment wheel 116 is rotated to lower support block 96, and thereby feeler wheel 124, by the predetermined distance, for example, 0.5 cm. In order to accurately ensure that idler wheel 124 is only moved along the z-axis for the predetermined distance, a scale 132 may be fixedly secured to rod 92 by upper and lower collars 134 and 136, respectively. Alternatively, a motor may be provided with corresponding circuitry for automatically performing the manual operation effected through adjustment wheel 116. Still further, scale 132 may be eliminated and a circuit 150 secured to rod 92 may be provided for automatically providing an output signal corresponding to the z-axis component. In such case, for example, a reciprocable rod 152 can be provided which extends into contact with support block 96 at one end and the other end of which adjusts a potentiometer or LVDT setting within circuit 150. After feeler wheel 124 is moved along the z-axis direction for 0.5 cm., the tracing operation along the x-y plane is again effected. This operation is repeated until the entire facial swelling 56 has been traced in such manner.

Figure 4:
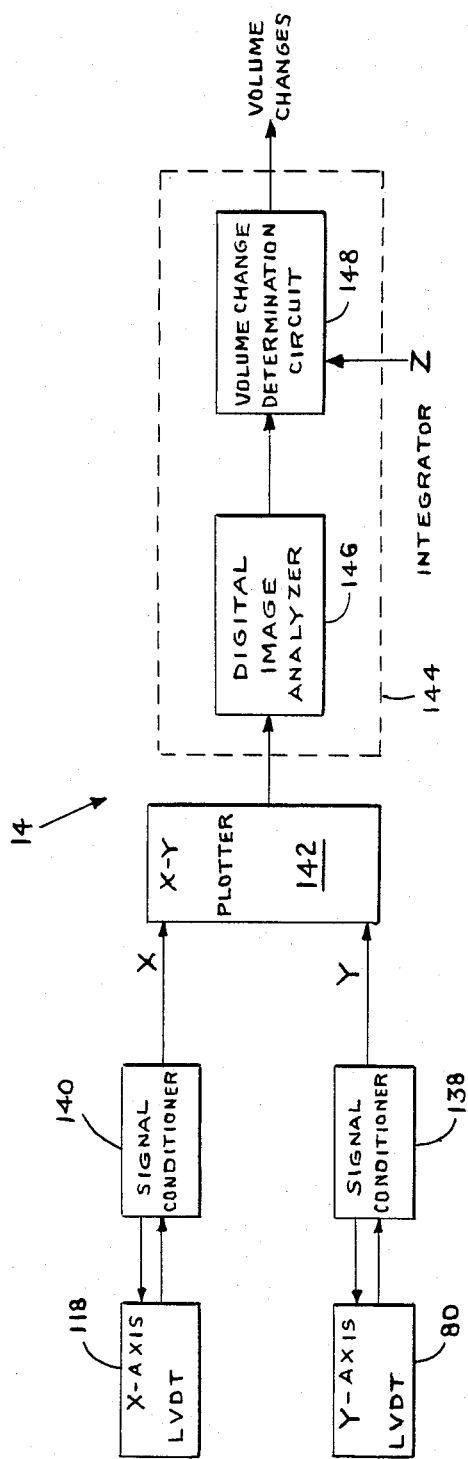
FIG. 4 is a block diagram of circuitry which forms part of the present invention and which is used in conjunction with the apparatus of FIG. 1.

Referring now to FIG. 4, circuitry 14 for use with the apparatus of FIG. 1 includes first and second signal conditioners 138 and 140 connected with y-axis LVDT 80 and x-axis LVDT 118, respectively. Signal conditioners 138 and 140 provide the excitation voltage to the primary winding of the respective LVDT to change the amplification of the output signal, that is, to provide a gain adjustment. In other words, signal conditioners 138 and 140 set the input power to the respective LVDT. In addition, signal conditioners 138 and 140 rectify the AC signal from the respective LVDT to produce a DC output signal which is supplied to respective Y and X inputs of an X-Y plotter 142. In addition, signal conditioners 138 and 140 permit a zero-shift operation to change the range of the output levels therefrom.

X-Y plotter 142, in response to the output signals from signal conditioners 138 and 140, provides a graphical representation of the tracing by feeler wheel 124. In accordance with the present invention, a pre-operative and post-operative graph is obtained for each tracing of feeler wheel 124 at the same vertical or z-axis position. Accordingly, X-Y plotter 142 graphs two curves on the same paper, at different times, which curves are connected at the respective ends thereof, that is, corresponding to points where there is no facial swelling. As a result, an area is defined between the pre-operation and post-operation graphs. A plurality of such graphs are provided for different z-axis settings, an area being defined for each z-axis setting. Plots for each z-axis setting are supplied to an effective integrator 144 which provides an approximate three-dimensional integration of the series of contours to provide a volume change between post-operation and pre-operation contours. In particular, integrator 144 may include a digital image analyzer 146 which analyzes the graphs from X-Y plotter 142 for each z-axis setting to provide an output signal corresponding to the differential area between the post-operative and pre-operative graphs from X-Y plotter 142. Alternatively, it is to be appreciated that digital image analyzer 146 may be replaced by a planimeter. The output from digital image analyzer 146 is then supplied to a volume change determination circuit 148 which also receives a signal corresponding to the predetermined increment that feeler wheel 124 is successively moved along the z-axis. In response thereto, volume change determination circuit 148 provides a volume change output corresponding to the change in volume caused by the facial swelling. It is to be appreciated that volume change determination circuit may effectively be constituted by a multiplier which multiplies the signal corresponding to each differential area from digital image analyzer 146 by the predetermined distance along the z-axis, and then adds the resultant signals for each of the plots to produce the volume change output. It is to be appreciated, however, that other more sophisticated mathematical computations can be utilized to more exactly approximate the three-dimensional integration. Alternatively, X-Y plotter 142, digital image analyzer 146 and volume change determination circuit 148 may all be replaced by a microprocessor which, in accordance with a respective program supplied thereto, automatically computes the volume change output signal in accordance with the aforementioned discussion.

It is to be appreciated that various modifications can be made to the present invention within the scope of the claims herein. For example, although xyz coordinates have been utilized, $r\theta z$ coordinates may be used instead. Also, graphs may be compared for two post-operative times, rather than a post-operative time with the pre-operative time.

Having described a specific preferred embodiment of the invention with reference to the accompanying drawings, it is to be understood that the present invention is not limited to this specific embodiment and that various changes and modifications may be effected therein by one skilled in the art without departing from the scope and spirit of the invention as defined by the appended claims.

What is claimed is:

1. Apparatus for measuring a volume change for facial swelling of a person, comprising:
   bite fork means engageable within the mouth of said person for providing a relatively fixed reference position for said facial swelling;
   reciprocable means having a free end and reciprocable in a first direction substantially normal to said facial swelling;
   biasing means for maintaining said free end of said reciprocable means in communication with said facial swelling;
   scanning means for moving said reciprocable means in a second direction substantially normal to said first direction to cause said free end to trace across said facial swelling in a plurality of parallel planes spaced apart by a predetermined distance;
   first output means for producing a first signal in response to said reciprocable movement of said reciprocable means in said first direction;
   second output means for producing a second signal in response to movement of said free end in said second direction; and
   differential volume means for producing an output signal corresponding to said volume change in response to said first signal, said second signal and an input signal corresponding to said predetermined distance.

2. Apparatus according to claim 1; further comprising bite fork adjustment means for adjusting the position of said bite fork means.

3. Apparatus according to claim 2; further comprising support means; and in which said bite fork adjustment means includes slide means mounted on said support means and slidably movable in a third direction, bite fork post means mounted on said slide means, clamp means mounted on said bite fork post means for slidable movement in a fourth direction substantially normal to said third direction, and rod means mounted in said clamp means for slidable movement in a fifth direction substantially normal to said third and fourth directions and having a free end for supporting said bite fork means.

4. Apparatus according to claim 3; further including forehead support means having a forehead support, support block means slidably mounted on said bite fork post means for movement in said fourth direction, and second rod means slidably mounted in said support block means for movement in said fifth direction and having a free end for supporting said forehead support.

5. Apparatus according to claim 1; in which said first and second output means are each constituted by a linear variable differential transformer.

6. Apparatus according to claim 1; in which said reciprocable means includes feeler rod means having a free end, feeler wheel means rotatably mounted at said free end; and said biasing means includes spring means for biasing said feeler rod means in said first direction for maintaining said feeler wheel means in contact with said facial swelling.

7. Apparatus according to claim 1; further including support means; and in which said scanning means includes base plate means fixedly mounted on said support means, slide means mounted on said base plate means for sliding movement in said second direction, support rod means fixedly mounted on said slider means, and support block means slidably mounted on said support rod means and having said reciprocable means fixedly secured thereto.

8. Apparatus according to claim 7; further comprising means for successively moving said reciprocable means in a third direction substantially normal to said first and second directions by said predetermined distance.

9. Apparatus according to claim 7; further comprising potentiometer means for producing an output signal corresponding to said predetermined distance in response to slidable movement of said support block means on said support rod means.

10. Apparatus according to claim 1; in which said differential volume means includes X-Y plotter means supplied with both of said first and second signals at two different times for producing a graphical representation of a differential area of said facial swelling for each parallel plane traced across said facial swelling, and approximate three-dimensional integration means for producing said output signal corresponding to the volume change in response to said predetermined distance and said graphical representation from said X-Y plotter means for all of said traces across the facial swelling in said plurality of parallel planes.

11. Apparatus according to claim 10; in which said approximate three-dimensional integration means includes digital image analyzer means for producing an output signal corresponding to said differential area for each graphical representation from said X-Y plotter means and volume change determination means for producing said output signal in response to said output signal from said digital image analyzer means and a signal corresponding to said predetermined distance.

* * * * *